United States Patent [19]

Reader

[11] 3,932,566
[45] Jan. 13, 1976

[54] PHOSPHONATE POLYMERS
[75] Inventor: Arthur M. Reader, Waynesboro, Va.
[73] Assignee: Celanese Corporation, New York, N.Y.
[22] Filed: Sept. 16, 1974
[21] Appl. No.: 506,065

[52] U.S. Cl................ 260/930; 260/2 P; 260/45.85
[51] Int. Cl.$^2$............................................ C07F 9/40
[58] Field of Search..................... 260/930, 973, 2 P

[56] References Cited
UNITED STATES PATENTS
2,952,666   9/1960   Coover et al.................... 260/2 P X

*Primary Examiner*—Richard L. Raymond

[57] ABSTRACT

Novel thermoplastic polymers are provided by the interaction of bis(2-hydroxyethyl) terephthalate and a phosphonyl dihalide.

3 Claims, No Drawings

PHOSPHONATE POLYMERS

BACKGROUND OF THE INVENTION

The production of bis(hydroxyalkyl) esters of benzenedicarboxylic acids such as bis(2-hydroxyethyl) terephthalate has become of significant commercial importance in recent years because these diesters can be polymerized to form linear super polyesters. These polyesters such as polyethylene terephthalate are widely used in textiles, tire cord, and the like.

The present invention has developed from the investigation of new polymeric compositions derived from bis(2-hydroxyethyl) terephthalate which is now an inexpensive and readily available commercial product. It was deemed desirable to endeavor to introduce the excellent properties of bis(2-hydroxyethyl) terephthalate into polymeric compositions which would have unique properties and versatility in applications commonly served by polyester type thermoplastic resins.

Thus, it is an object of the present invention to provide novel polymers based on bis(2-hydroxyethyl) terephthalate.

It is another object of the present invention to provide polyester polymers which contain phosphorus.

It is still another object of the present invention to provide thermoplastic phosphonate polymers which are valuable as plasticizers for imparting flame retardancy to polyester plastics, or as additives for modifying the properties of resin compositions.

Other objects and advantages of the present invention will become apparent from the following description and examples.

DESCRIPTION OF THE INVENTION

One or more objects of the present invention are accomplished by a polymerization process which comprises reacting bis(2-hydroxyethyl) terephthalate with a phosphonyl dihalide having the formula:

wherein X is selected from chlorine, bromine and fluorine; and R is an organic radical containing between 1 and about 22 carbon atoms. The preferred phosphonyl dihalides are those wherein X is selected from chlorine and bromine; and R is selected from alkyl radicals containing between 1 and about 6 carbon atoms, and aryl radicals containing between 6 and about 10 carbon atoms.

In a preferred embodiment of the present invention, there is provided novel phosphonate polymers which can be characterized by the structural formula:

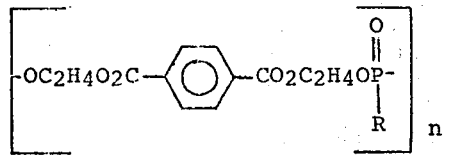

wherein R is selected from alkyl radicals containing between 1 and about 6 carbon atoms, and aryl radicals containing between 6 and about 10 carbon atoms; and n is an integer between 2 and about 10,000, and preferably between 5 and about 5,000. R can contain any chemical substituent (e.g., halogen, alkenyl, alkoxyl and nitro group) which does not interfere with the reaction between bis(2-hydroxyethyl) terephthalate and phosphonyl dihalide.

Illustrative of the phosphonyl dihalide reactants which can be employed are methylphosphonyl dichloride; methylphosphonyl dibromide; methylphosphonyl difluoride; methylphosphonyl chloride bromide; ethylphosphonyl dichloride; ethylphosphonyl dibromide; isopropyl phosphonyl dichloride; isopropenyl phosphonyl dibromide; butylphosphonyl dichloride; isobutylphosphonyl dibromide; amylphosphonyl dichloride; chlorohexylphosphonyl dichloride; phenylphosphonyl dichloride; bromophenylphosphonyl dibromide; tolylphosphonyl dichloride; xylylphosphonyl dichloride; naphthylphosphonyl dichloride; and the like.

There are a variety of known methods for producing the bis(2-hydroxyethyl) terephthalate reactant of the invention process. Probably best known and most widely used methods for producing these esters of benzenedicarboxylic acids are those in which the acid is suspended in an inert liquid medium and then reacted with an alkylene oxide in the presence of a catalyst. For example, see U.S. Pat. No. 3,037,049, May 29, 1962 to Alexander A. Vaitekunas which discloses the use of such liquid reaction medium as aromatic hydrocarbons, ketones and dioxane and which also discloses the use of tertiary amine catalysts. Also, such patents as Belgian Pat. No. 666,527, Belgian Pat. No. 660,257, British Pat. No. 999,242, British Pat. No. 1,029,669, German Pat. No. 1,157,623, French Pat. Nos. 1,415,134, 1,430,842, 1,408,874 and Netherlands Pat. Nos. 6,413,334, 6,506,220 and 6,508,415 disclose esterification processes wherein various reaction media such as hydrocarbons, halohydrocarbons, water, alcohols, nitriles and dimethylformamide-water are disclosed and wherein such catalysts as phosphines, arsines, quaternary ammonium compounds, stibines, amino acids, alkali sulfites, alkali chlorides and alkali nitrates are used as catalysts. More recent advances in methods for producing bis(2-hydroxyethyl) terephthalate are described in U.S. Pat. Nos. 3,584,031; 3,644,484; and 3,597,471.

The syntheses of phosphonyl dihalides is in one method accomplished by aeration of a hydrocarbon or mixtures thereof in the presence of phosphorus trichloride:

$$RH + PCl_3 + (O) \rightarrow RP(O)Cl_2 + HCl$$

A review of synthesis methods is found in "Organophosphorus Compounds" by G. M. Kosolapoff (John Wiley & Sons, New York, 1950).

In producing the phosphonate polymers of the present invention, it is advantageous first to dissolve the bis(2-hydroxyethyl) terephthalate and phosphonyl dihalide reactants in an inert common solvent for the two reactants before adding one of the reactants to the other reactant. Suitable inert solvents for the two reactants are benzene, toluene, chloroform, dialkyl ethers of alkylene glycols, dioxane, tetrahydrofuran, hexane, dichlorobenzene, and the like.

The bis(2-hydroxyethyl) terephthalate and phosphonyl dihalide reactants are conveniently reacted in approximately equimolar quantities. A molar excess of either reactant can be employed if it has the effect of accelerating the polymerization reaction to completion.

The reaction temperature is not critical, and generally will range between about 0°C. and 150°C. It is preferred to mix the reactants at a temperature below 25°C. and subsequently to conduct the reaction at a temperature between 50° C. and 100°C. Since mose of the reactions are exothermic, external cooling of the reaction vessel usually is necessary.

When the reactants combine, a hydrogen halide is produced as a reaction product. It is desirable to remove this by-product with a hydrogen halide remover to promote the reaction and to eliminate any side reactions which might be caused by the presence of the hydrogen halide. The hydrogen halide by-product can be removed by various known techniques. One technique is to pass an inert gas, such as nitrogen, through the reaction mixture. When this procedure for removing the hydrogen halide from the batch is used, the removal of the liberated hydrogen halide may be facilitated by carrying out the reaction at reduced pressure. Another method for removing the hydrogen halide which has been found useful in the practice of this invention is to chemically combine the hydrogen halide with a hydrogen halide acceptor, such as pyridine, triethyl amine, dimethyl aniline and the like. An amount of hydrogen halide acceptor just necessary to combine with the liberated hydrogen halide is sufficient. In practice, it generally is preferred to use a slight excess of the hydrogen halide acceptor to insure that there is a sufficient amount of the acceptor in the charge to combine with all of the hydrogen halide produced by the reaction.

The phosphonate polymer formed by the reaction of bis(2-hydroxyethyl) terephthalate and phosphonyl dihalide, depending on the molecular weight of the polymer will in some cases precipitate out as a solid during the course of the polymerization reaction. This polymeric solid can be freed of hydrogen halide acceptor salt if present by water washing of the polymeric solid. In the cases where the phosphonate polymer remains dissolved in the solvent medium, the hydrogen halide acceptor salt is removed by filtration or decantation. The solvent medium can be removed by distillation, and the polymer collected as a residue. Or, a non-solvent for the phosphonate polymer can be added to the solvent medium to precipitate the polymer product.

The phosphonate polymers of the present invention have high thermal stability, and are useful as flame resistant materials, and as additives for imparting flame retardancy to plastics, lubricants, hydraulic fluids, and the like. They are generally self-extinguishing when used in shaped articles. They may be used as additives to improve the flame retardancy of polyester fibers and other synthetic fibers, particularly for applications such as carpets and children's blankets.

The following examples are further illustrative of the present invention. The reactants and other specific ingredients are presented as being typical, and various modifications can be devised in view of the foregoing disclosure within the scope of the invention.

EXAMPLE 1

Preparation of Bis(2-hydroxyethyl) Terephthalate

A 3-liter stirred autoclave is charged with 600 grams of crude terephthalic acid (3.61 moles), 1600 ml. of 2-propyldioxolane reaction medium, 0.11 mole of tetraethyl ammonium terephthalate catalyst and then purged with nitrogen. Liquid ethylene oxide (473 grams, 10.75 mole) is then pumped in and the reactor heated quickly to 155°C. by passing steam through internal coils. After about 3½ minutes, the reaction is terminated by pressuring the contents of the autoclave into a vessel where the ethylene oxide is flashed and then the unreacted terephthalic acid removed by filtration. Cooling of the filtrate to about 18°C. gives about 742 grams of crude bis(2-hydroxyethyl) terephthalate.

EXAMPLE 2

Preparation of Catalyst For Bis(2-hydroxyethyl) Terephthalate Synthesis

A catalyst is prepared from Montrek 600E by mixing 24 grams of the material with 19.5 grams of terephthalic acid as well as 30 ml. of water so that good mixing can be obtained. After stirring the mixture for about 1 hour, it is placed on a rotary film evaporator for the removal of the water and a thick solid is recovered which is the terephthalic acid salt of the hydroxyethylated polyethyleneimine. Montrek 600E is Dow Chemical Company's designation for a 40 percent aqueous solution of hydroxyethylated polyethyleneimine which is prepared by reacting polyethyleneimine having a molecular weight of about 40,000 to 60,000 with ethylene oxide.

EXAMPLE 3

Preparation of Bis(2-hydroxyethyl) Terephthalate

A 3-liter stirred autoclave is charged with 600 grams (3.6 moles) of fiber grade terephthalic acid, 1600 ml. chlorobenzene, 12.4 grams of the terephthalic acid salt of hydroxyethylated polyethyleneimine as prepared in Example 2, and then purged with nitrogen. Liquid ethylene oxide (8.6 moles) is then pumped in and the reactor heated to 175°C. by passing steam through internal coils. The temperature is maintained at 175°C. for about 30 minutes with the pressure varying during the period from about 215 p.s.i.g. at the beginning of the period to 80 p.s.i.g. at the end of the period. After the thirty-minute period, the reaction is terminated by pressuring the contents of the autoclave into a vessel where ethylene oxide is flashed and then the unreacted terephthalic acid and other solids removed by filtration. Cooling of the filtrate to about 30°C. yields about 760 grams of bis(2-hydroxyethyl) terephthalate (dry basis). Conversion of the terephthalic acid charged to the diester product is about 91 mole percent.

EXAMPLE 4

Preparation of Phosphonate Polymer

To a flask equipped with a stirrer and a nitrogen flushing system, bis(2-hydroxyethyl) terephthalate (2.1 moles), pyridine (4.2 moles) and 150 ml. benzene are added. A solution of methylphosphonyl dichloride (2 moles) in 200 ml. of benzene is then added to the flask over a period of 20 minutes at a temperature below 25°C. with stirring. The temperature during the addition is maintained with the aid of external cooling of an ice bath.

After the addition is completed, the reaction mixture is stirred at 60°C. for 2 hours, then the reaction mixture is cooled to 25°C., and the solid precipitate is collected by filtration. The solid precipitate is washed with benzene, acetone and then with water. After drying under vacuum, the phosphonate polymer is recovered as a fine powder.

EXAMPLE 5

Preparation of Phenylphosphonyl Dichloride

Phosphorus trichloride is added to a vessel containing benzene. A stirrer, thermometer, reflux condenser and a fritted air inlet tube are fitted. Air is swept through the vessel vigorously with constant stirring at a temperature of about 80°C. The reaction is continued for three hours and a yield of phenylphosphonyl dichloride of about 75% of the theoretical based on phosphorus trichloride is obtained.

Aldrich Chemical Company supplies this chemical under the name phenylphosphonic dichloride.

EXAMPLE 6

Preparation of Phosphonate Polymer

Following the general procedure of Example 4, bis(2-hydroxyethyl) terephthalate (0.6 mole), pyridine (1.1 mole) and 50 ml. benzene are added to the reaction flask. A solution of phenylphosphonyl dichloride (0.5 mole) in 100 ml. of benzene is then added to the flask, with external cooling of the reaction flask.

The reaction mixture is stirred at 75°C. for 30 minutes, and then allowed to cool to room temperature. The pyridine hydrochloride salt is removed by filtration.

The benzene filtrate is diluted with an equal volume of acetone-ethanol (50/50) to precipitate the phosphonate polymer. After benzene, acetone and water washes, the phosphonate polymer is recovered as a soft waxy solid.

What is claimed is:

1. A class of phosphonate polymers characterized by the structural formula:

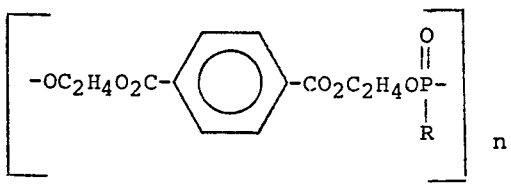

wherein R is selected from alkyl and substituted alkyl radicals containing between 1 and about 6 carbon atoms, the substituents being selected from halogen, alkenyl, alkoxyl and nitro groups, and aryl and substituted aryl radicals containing between 6 and about 10 carbon atoms, the substituents being selected from halogen, alkoxyl and nitro groups; and $n$ is an integer between 5 and about 5,000.

2. A phosphonate polymer in accordance with claim 1 wherein R is a methyl radical.

3. A phosphonate polymer in accordance with claim 1 wherein R is a phenyl radical.

* * * * *